United States Patent [19]
Spears

[11] Patent Number: 5,814,490
[45] Date of Patent: Sep. 29, 1998

[54] AMPLIFICATION AND DETECTION OF CHLAMYDIA TRACHOMATIS NUCLEIC ACIDS

[75] Inventor: Patricia A. Spears, Raleigh, N.C.

[73] Assignee: Becton, Dickinson and Company, Franklin Lakes, N.J.

[21] Appl. No.: 661,507

[22] Filed: Jun. 11, 1996

[51] Int. Cl.$^6$ ............... C12P 19/34; C12Q 1/68; C07H 21/04; C07M 21/00
[52] U.S. Cl. ............ 435/91.2; 435/6; 436/24.3; 436/25.32
[58] Field of Search ............... 536/24.3, 25.32; 435/91.2, 6, 810

[56] References Cited

U.S. PATENT DOCUMENTS

| | | | |
|---|---|---|---|
| 4,563,419 | 1/1986 | Ranki et al. | 435/6 |
| 5,232,829 | 8/1993 | Longiaru et al. | |

FOREIGN PATENT DOCUMENTS

| | | | |
|---|---|---|---|
| 0 336 412 | 10/1989 | European Pat. Off. | |
| 0 336 412 A2 | 10/1989 | European Pat. Off. | C12Q 1/68 |
| 0 499 681 | 8/1992 | European Pat. Off. | |
| 0 499 681 A1 | 8/1992 | European Pat. Off. | C12N 15/30 |
| WO 93/00447 | 1/1993 | WIPO. | |

OTHER PUBLICATIONS

M. Bassiri, et al. "Detection of Chlamydia trachomatis in Urine Specimens from Women by Ligase Chain Reaction" *J. Clin. Microbiol.* 33:898–900 (1995).

M. Domeika, et al. "Diagnosis of Genital Chlamydia trachomatis Infections in Asymptomatic Males by Testing Urine by PCR" *J. Clin. Microbiol.* 32:2350–2352 (1994).

M. A. Chernesky, et al. "diagnosis of Chlamydia trachomatis Infections in Men and Women by Testing First–Void Urine by Ligase Chain Reaction" *J. Clin. Microbiol.* 32:2682–3685 (1994).

H. H. Lee, et al. "Diagnosis of Chlamydia trachomatis gentiourinary infection in women by ligase chain reaction assay of urine" *Lancet* 345:213–16 (1995).

J. E. Bauwens, et al. "Diagnosis of Chlamydia trachomatis Urethritis in Men by Polymerase Chain Reaction Assay of First–Catch Urine" *J. Clin. Microbiol.* 31:3013–3106 (1993).

R. Warren, et al. "Comparative Evaluation of Detection Assays for Chlamydia trachomatis" *J. Clin. Microbiol.* 31:1663–1666 (1993).

J. E. Horn, et al. "Use of Nucleic Acid Probes for the Detection of Sexually Transmitted Infectious Agents" *Diagn. Microbiiol Infect. Dis.* 4:101S–109S (1986).

L. Palmer and S. Falkow "A Common Plasmid of Chlamydia trachomatis" *Plasmid* 16:52–62 (1986).

G. T. Walker, et al. "Strand displacement amplificatioin–an isothermal, in vitro DNA amplification technique" *Nucl. Acids Res.* 20:1691–1696 (1992).

G. T. Walker, et al. "Isothermal in vitro amplification of DNA by a restriction enzyme/DNA polymerase system" *Proc. Natl. Acad. Sci. USA* 89:392–396 (1992).

(List continued on next page.)

*Primary Examiner*—Kenneth R. Horlick
*Assistant Examiner*—Joyce Tung
*Attorney, Agent, or Firm*—Donna R. Fugit

[57] ABSTRACT

Amplification primers useful in assays for species-specific detection of a target sequence in the cryptic plasmid of *C. trachomatis* are described. The primers of the invention amplify a target in the region of nucleotides 2219–2366 of the cryptic plasmid sequence, and the target binding sequences disclosed may be adapted for use in amplification primers for a variety of amplification reactions.

23 Claims, 2 Drawing Sheets

OTHER PUBLICATIONS

G. T. Walker, et al. "DNA detection by strand displacement amplification and fluorescence polarization with signal enhancement using a DNA binding protein" *Nucl. Acids Res.* 24:348–353 (1996).

G. T. Walker, et al. "Strand displacement amplification (SDA) and transient–state fluorescence polarization with signal detection of Mycobacterium tuberculosis DNA" *Clin. Chem.* 42:9–13 (1996).

E. M. Peterson and L. M. De la Maza "Characterization of Chlamydia DNA by Restriction Endonuclease Cleavage" *Infect. Immun.* 41:604–608 (1983).

T. Hyypia, et al. "Analysis and Detection of Chlamydial DNA" *J. Gen. Microbiol.* 130:3159–3164 (1984).

T. Hyypia, et al. "Detection of Chlamydia trachomatis in Clinical Specimens by Nucleic Acid Spot Hybridization" *J. Gen. Microbiol.* 131:975–978 (1985).

T. Joseph, et al. "Molecular Characterization of Chlamydia trachomatis and Chlamydia psittaci Plasmids" *Infect. Immun.* 51:699–703 (1986).

K. S. Sriprakash and E. S. Macavoy "Characterization and Sequence of a Plasmid from the Trachoma Biovar of Chlamydia trachomatis" *Plasmid* 18:205–214 (1987).

C. Hatt, et al. "Analysis of the entire nucleotide sequence of the cryptic plasmid of Chlamydia trachomatis serovar LI. Evidence of involvement in DNA replication" *Nucl. Acids Res.* 16:4053–4067 (1988).

M. Comanducci, et al. "The structure of a plasmid of Chlamydia trachomatis believed to be required for growth within mammalian cells" *Molec. Microbiol.* 2:531–538 (1988).

Walker et al. Strand Displacement Amplification an isothermal, in vitro DNA Amplification Technique, Nucleic Acid Research, vol. 20(7), pp. 1691–1696, 1992.

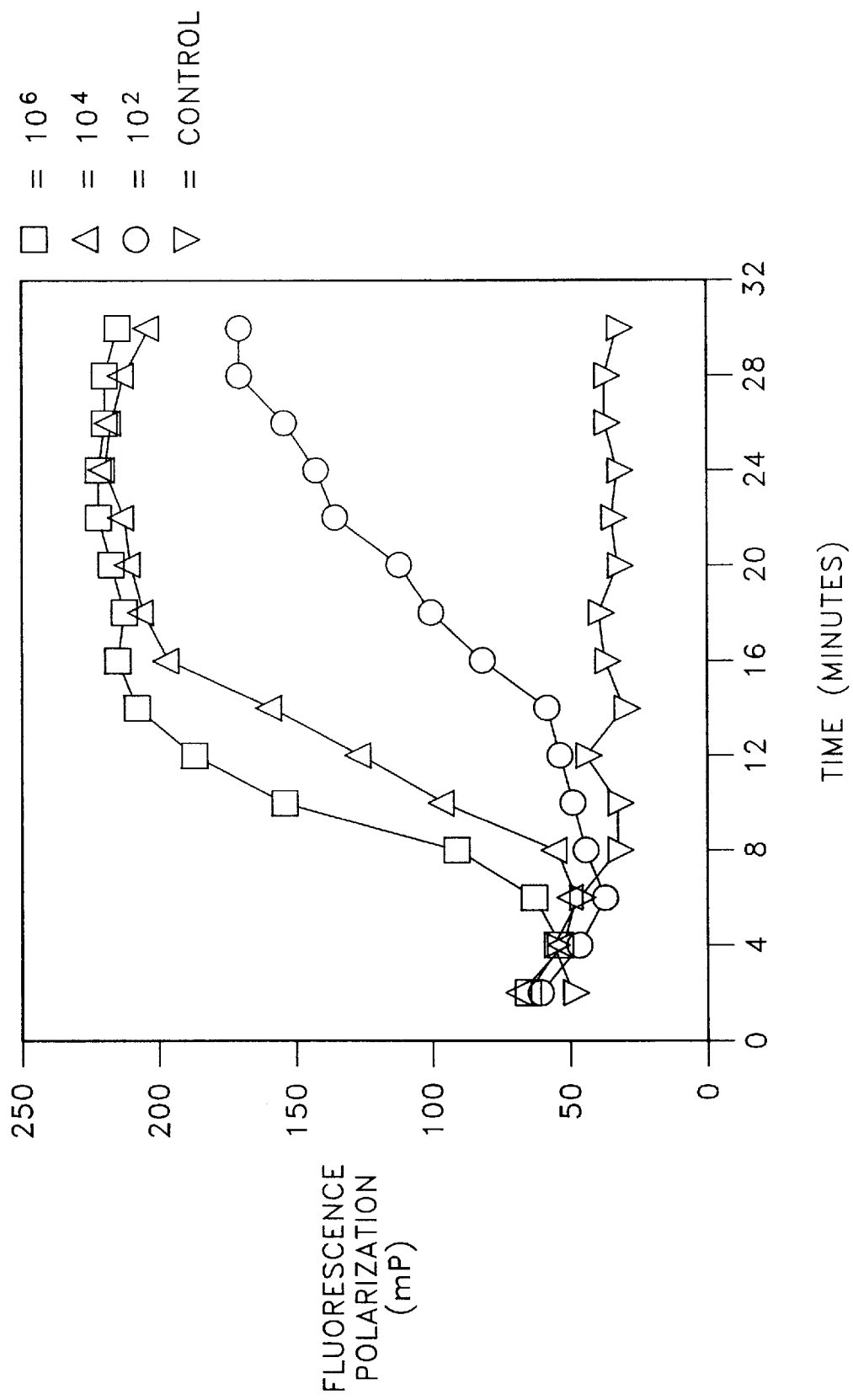

AMPLIFICATION AND DETECTION OF CHLAMYDIA TRACHOMATIS NUCLEIC ACIDS

FIELD OF THE INVENTION

The invention relates to nucleic acid amplification, including detection and/or identification of microorganisms using nucleic acid amplification.

BACKGROUND OF THE INVENTION

*Chlamydia trachomatis* is a major cause of urogenital infections in both males and females in the United States. The in vivo diagnosis of Chlamydia requires culture on McCoy cell monolayers, which is labor intensive and requires approximately 48–72 hours. Several more rapid tests have been developed based on antigen detection by direct fluorescent antibody staining (DFA), enzyme immunoassays (EIA) and enzyme-linked immunosorbent assays (ELISA). A probe hybridization assay for direct detection of Chlamydia (PACE2, GenProbe, see Warren, et al. 1993. *J. Clin. Microbiol.* 31:1663–1666.) has also been developed. Most of these currently available tests require endocervical swabs in females and urethral swabs in males. However, DNA amplification technologies such as PCR, LCR and SDA have the potential to provide highly sensitive alternatives for Chlamydia detection using less invasive clinical specimens such as urine. Domeika et al. (1994. *J. Clin. Microbiol.* 32:2350–2352), Bauwens, et al. (1993. *J. Clin. Microbiol.* 31:3013–3106), and U.S. Pat. No. 5,232,829 report amplification of *Chlamydia trachomatis* DNA using the PCR, followed by microtiter plate hybridization detection. Amplification tests which use the LCR followed by microparticle sandwich immunoassay detection have also been reported (Chernesky et al. 1994. *J. Clin. Microbiol.* 32:2682–2685, Lee et al. 1995. *Lancet* 345:213–216, Bassiri et al. 1995 *J. Clin. Microbiol.* 33:898–900). Currently, these tests take 4–6 hours to complete.

The cryptic plasmid of *Chlamydia trachomatis* is a 7.4 kb plasmid which is specific to this organism. It is present in about 10 copies per genome equivalent and detects all 200 clinical strains of *C. trachomatis* when used as a hybridization probe (Palmer and Falkow. 1986. *Plasmid* 16:52–62). Hatt, et al. (1988. *Nucl. Acids Res.* 16:4053–4067) reported the sequence of the cryptic plasmid of the L1 serovar, and EP 0 499 681 describes the sequence of the cryptic plasmid of serotype D. The sequence of the cryptic plasmid of *C. trachomatis* L2/434/Bu is shown in EP 0 336 412, which also describes oligonucleotide probes derived from this cryptic plasmid sequence. One embodiment of the plate capture assay described in U.S. Pat. No. 5,232,829 is directed to detection of cryptic plasmid target sequences. Two amplification primer sets are described: one which produces a 208 base pair amplicon using primers which hybridize at positions 195–219 and 377–402, and a second which produces a 173 base pair amplicon using primers which hybridize to positions 678–700 and 827–850. In one example, WO 93/00447 describes gap-filling LCR for detection of Chlamydia target sequences. The oligonucleotides employed are based on map positions 6693.1, 6693.2, 6693.3 and 6694.4 of Hatt, et al., supra.

The following terms are defined herein as follows:

An amplification primer is a primer for amplification of a target sequence by extension of the primer after hybridization to the target sequence. The 3' end of an SDA amplification primer (the target binding sequence) hybridizes at the 3' end of the target sequence. The target binding sequence is about 10–25 nucleotides in length and confers hybridization specificity on the amplification primer. The SDA amplification primer further comprises a recognition site for a restriction endonuclease 5' to the target binding sequence. The recognition site is for a restriction endonuclease which will nick one strand of a DNA duplex when the recognition site is hemimodified, as described by G. Walker, et al. (1992. *PNAS* 89:392–396 and 1992 *Nucl. Acids Res.* 20:1691–1696). The about 10–25 nucleotides 5' to the restriction endonuclease recognition site (the "tail") function as a polymerase repriming site when the remainder of the amplification primer is nicked and displaced during SDA. The repriming function of the tail nucleotides sustains the SDA reaction and allows synthesis of multiple amplicons from a single target molecule. The sequence of the tail is generally not critical and can be routinely selected and modified to obtain the desired $T_m$ for hybridization. As the target binding sequence is the portion of a primer which determines its target-specificity, for amplification methods which do not require specialized sequences at the ends of the target the amplification primer generally consists essentially of only the target binding sequence. For amplification methods which require that specialized sequences other than the nickable restriction site and primer tail of SDA be appended to the target (e.g., an RNA polymerase promoter for 3SR, NASBA or transcription based amplification), the required specialized sequence may be linked to the target binding sequence using routine methods for preparation of oligonucleotides without altering the hybridization specificity of the primer.

A bumper primer or external primer is a primer used to displace primer extension products in isothermal amplification reactions. The bumper primer anneals to a target sequence upstream of the amplification primer such that extension of the bumper primer displaces the downstream amplification primer and its extension product.

The terms target or target sequence refer to nucleic acid sequences to be amplified. These include the original nucleic acid sequence to be amplified and its complementary second strand and either strand of a copy of the original sequence which is produced by the amplification reaction.

Copies of the target sequence which are generated during the amplification reaction are referred to as amplification products, amplimers or amplicons.

The term extension product refers to the copy of a target sequence produced by hybridization of a primer and extension of the primer by polymerase using the target sequence as a template.

The term species-specific refers to detection, amplification or oligonucleotide hybridization in a species of organism or a group of related species without substantial detection, amplification or oligonucleotide hybridization in other species of the same genus or species of a different genus. *C. trachomatis*-specific detection, amplification or hybridization refers to species-specificity for *C. trachomatis*.

The term assay probe refers to any oligonucleotide used to facilitate detection or identification of a nucleic acid. For example, in the present invention, assay probes are used for detection or identification of *C. trachomatis* nucleic acids, either directly or after amplification. Detector probes, capture probes and signal primers are examples of assay probes.

SUMMARY OF THE INVENTION

Primers for species-specific detection of a target sequence in the cryptic plasmid of *C. trachomatis* are described. The amplification primers of the invention amplify a target in the region of nucleotides 2219–2366 of the cryptic plasmid sequence. Preferred amplification primers comprise the specialized sequences required for SDA, however, amplification primers with similar specificity may be constructed using the disclosed target binding sequences and, optionally, other sequences required for a selected amplification reaction.

DESCRIPTION OF THE DRAWINGS

FIG. 2 is a graph showing real-time detection of target amplification using the primers of the invention.

Figure 1:
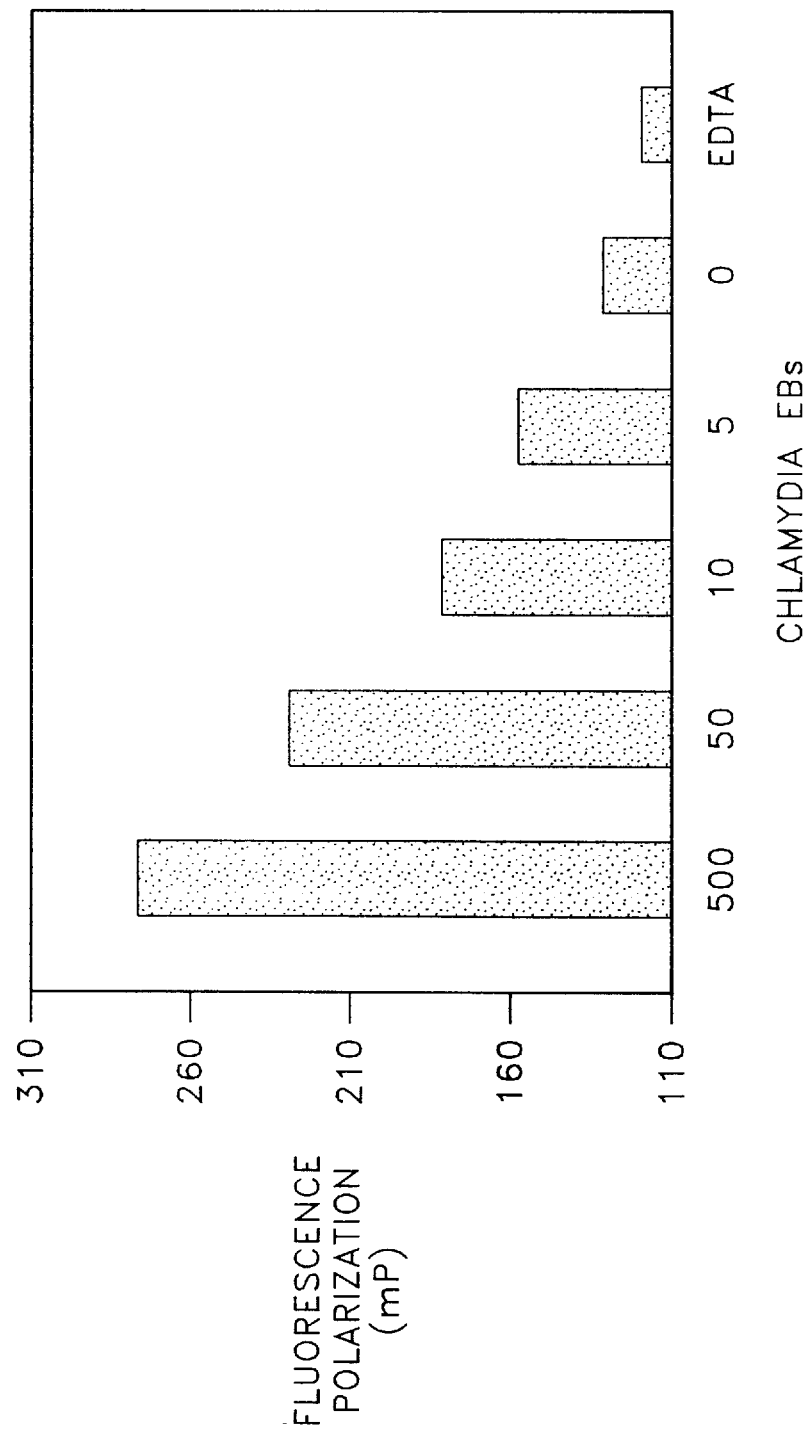
FIG. 1 is a graph illustrating the results of Example 3, showing a detection sensitivity of 5 elementary bodies using the oligonucleotides of the invention.

DETAILED DESCRIPTION OF THE INVENTION

To identify potential target binding sequences for use in amplification primers, the nucleotide sequence of the cryptic plasmid of *C. trachomatis* (GenBank Accession #X06707) was analyzed for open reading frames with low GC content and no runs of three consecutive Cs or Gs. A potential target in the region of nucleotides 2219–2366 (bumper to bumper in the exemplified SDA reactions) was identified by these criteria (GC content about 34%). Target binding sequences for three upstream amplification primers (SEQ ID NO:1–3) and two downstream amplification primers (SEQ ID NO:4–5) were selected, and amplification primers for SDA comprising these target binding sequences were synthesized by conventional methods. The amplification primers are shown below, with the target binding sequences italicized and the nickable restriction endonuclease recognition site bolded:

SEQ ID NO:1(S1.1)
ACCGCATCGAATCGATGTCTCGGG*TAGAAAATCGCATGCAAGATA*

SEQ ID NO:2(S1.2)
ACCGCATCGAATCGATGTCTCGGG*CGCATGCAAGATATCGAGTAT*

SEQ ID NO:3(S1.3)
ACGCCATCGAATCGATGTCTCGGG*ATGCAAGATATCGAGTATGCG*

SEQ ID NO:4(S2.1)
CGATTCCGCTCCAGACTTCTCGGG*AGCTGCCTCAGAATATACTCAG*

SEQ ID NO:5(S2.2)
CGATTCCGCTCCAGACTTCTCGGG*GCAAGCTGCCTCAGAATATAC*

For testing in SDA, a pair of bumper primers useful with all pairwise combinations of upstream and downstream amplification primers was also designed:

SEQ ID NO:6(B1)
TAAACATGAAAACTCGTTCCG

SEQ ID NO:7(B2)
TTTTATGATGAGGAACACTTAAACTCA

For detection of the amplification products, a detector probe which hybridized to the amplification products of all pairwise combinations of upstream and downstream amplification primers was selected:

SEQ ID NO:8(D1)
TAGAGTCTTCAAATATCAGAGCTTTACCTAACAA

The target binding sequences of the amplification primers confer *C. trachomatis* hybridization specificity and therefore provide the species-specificity of the assay. By way of example, the amplification primers listed above contain a recognition site for the restriction endonuclease BsoBI which is nicked during the SDA reaction. It will be apparent to one skilled in the art that other nickable restriction endonuclease recognition sites may be substituted for the BsoBI recognition site, including but not limited to those recognition sites disclosed in EP 0 684 315. Preferably, the recognition site is for a thermophilic restriction endonuclease so that the amplification reaction may be performed under optimum temperature conditions. Similarly, the tail sequence of the amplification primer (5' to the restriction endonuclease recognition site) is generally not critical, although it is important to avoid including the restriction site used for SDA and to avoid sequences which will hybridize either to their own target binding sequence or to other primers. Amplification primers for SDA according to the invention therefore consist of the 3' target binding sequences indicated above, a nickable restriction endonuclease recognition site 5' to the target binding sequence and a tail sequence about 10–25 nucleotides in length 5' to the restriction endonuclease recognition site. The length of the tail depends on the $T_m$ of the selected sequence, and can be easily adjusted by one skilled in the art to obtain sufficient hybridization. The tail sequence and the restriction endonuclease recognition site are sequences required for amplification by SDA. Other embodiments of amplification primers according to the invention consist of 1) the target binding sequence alone when no additional specialized sequence is required by the selected amplification reaction (e.g., the PCR), or 2) the target binding sequence and the additional sequences required for the amplification reaction (e.g., the RNA polymerase promoter required for amplification by 3SR or NASBA).

Amplification products may be detected by hybridization to an assay probe. The assay probe may be tagged with a detectable label to facilitate its detection when hybridized to the amplification product. The detectable label may be conjugated to the probe after it is synthesized or it may be incorporated into the probe during synthesis, for example in the form of a label-derivatized nucleotide. Such labels are known in the art and include directly and indirectly detectable labels. Directly detectable labels produce a signal without further chemical reaction and include such labels as fluorochromes, radioisotopes and dyes. Indirectly detectable labels require further chemical reaction or addition of reagents to produce the detectable signal. These include, for example, enzymes such as horseradish peroxidase and alkaline phosphatase, ligands such as biotin which are detected by binding to label-conjugated avidin, and chemiluminescent molecules. The assay probes may be hybridized to their respective amplification products in solution, on gels, or on solid supports. Following hybridization, the signals from the associated labels are developed, detected and optionally quantitated using methods appropriate for the selected label and hybridization protocol. The amount of signal detected for each amplification product may be used to indicate the relative amount of amplification product present. Ligand labels may also be used on assay probes to facilitate capture of the hybrid on a solid phase (capture probe).

An alternative method for detecting amplification products is by polymerase extension of a primer specifically hybridized to the target sequence. The primer is labeled as described above, for example with a radioisotope, so that the label of the primer is incorporated into the extended reaction product. This method is described by Walker, et al. (1992) *Nuc. Acids Res.* and *PNAS,* supra. Another method for detecting amplified target and control sequences is a chemiluminescent method in which amplified products are detected using a biotinylated capture probe and an enzyme-conjugated detector probe as described in U.S. Pat. No. 5,470,723. After hybridization of these two assay probes to different sites in the assay region of the target sequence, the complex is captured on a streptavidin-coated microtiter plate, and the chemiluminescent signal is developed and read in a luminometer. As another alternative for detection of amplification products, a signal primer (essentially a detector probe which is extended by polymerase, displaced and rendered double-stranded in a target amplification-dependent manner) as described in EP 0 678 582 may be included in an SDA reaction. In this embodiment, labeled secondary amplification products are generated during SDA in a target amplification-dependent manner and may be detected as an indication of target amplification.

SDA reactions employing the primers of the invention may incorporate thymine as taught by Walker, et al., supra, or they may wholly or partially substitute 2'-deoxyuridine 5'-triphosphate (dUTP) for TTP in the reaction, as taught in EP 0 624 643, to reduce cross-contamination of subsequent SDA reactions. dU (uridine) is incorporated into amplification products of both target and control sequences and can be excised by treatment with uracil DNA glycosylase (UDG). These abasic sites render the amplification product unamplifiable in subsequent SDA reactions. UDG may be inactivated by uracil DNA glycosylase inhibitor (Ugi) prior to performing the subsequent amplification to prevent excision of dU in newly-formed amplification products.

The primers or probes for performing the assay methods of the invention may be packaged in the form of a diagnostic kit for species-specific amplification or detection of *C. trachomatis* DNA. Kits for amplification may comprise amplification primers comprising the described target binding sequences for amplification of the *C. trachomatis* target sequence and, optionally, the reagents required for performing the selected amplification reaction (e.g., deoxynucleoside triphosphates, enzymes, buffers, polymerase, additional primers, etc.). The kits for target sequence amplification may further optionally include assay probes useful for detecting or identifying the amplified *C. trachomatis* target sequence, and/or an internal control sequence to be co-amplified with the target sequences as described in U.S. Pat. No. 5,457,027. Assay probes for detection of the amplified target may comprise a detectable label as described herein, and, optionally, the kits may include reagents for hybridization and/or detection of the assay probe.

EXAMPLE 1

The six pairwise combinations of the upstream and downstream amplification primers described above were tested in tSDA reactions essentially as described in EP 0 684 315. The 50 µl amplification reactions contained 5 mM $MgCl_2$, 0.2 mM each dGTP, dATP and TTP, 1.4 mM α-thio-dCTP, 10 ng/µl human placental DNA, 35 mM $K_iPO_4$ pH 7.6, 10% (v/v) glycerol, 0.5 µM SEQ ID NO:1, SEQ ID NO:2, or SEQ ID NO:3, 0.5 µM SEQ ID NO:4 or SEQ ID NO:5, 0.05 µM SEQ ID NO:6 and SEQ ID NO:7, 3.2 units/µl BsoBI (New England BioLabs), 0.125 unit/µl exonuclease deficient Bst DNA polymerase (Molecular Biology Resources) and $10^5$ or $10^3$ *C. trachomatis* elementary bodies (EBs). Prior to addition of BsoBI, Bst polymerase and $MgCl_2$, the reactions were heated at 95° C. for 5 min. to denature the target DNA. After denaturing the target, the samples were allowed to equilibrate at 53.5° C. for 5 min. Amplification was initiated by addition of 10 µl of enzyme mix (5 µl 50 mM $MgCl_2$, 0.5 µl of 25 units/µl Bst polymerase, 1 µl of 160 units/µl BsoBI and 3.5 µl 1X NEB2 buffer). After 30 min. of amplification at 53.5° C., 5 µl of each reaction was assayed for amplification products by hybridization of $^{32}$P-labeled SEQ ID NO:8 and primer extension as described by Walker, et al (1992. *Nucl. Acids Res.*, supra). The products were separated by 8% polyacrylamide gel electrophoresis and analyzed by autoradiography.

All amplification primer pairs containing SEQ ID NO:1 or SEQ ID NO:3 as the upstream primer produced readily detectable amplification products. In contrast, primer pairs containing SEQ ID NO:2 as the upstream primer performed poorly. Quantitation of the bands of the autoradiographs showed that amplification of $10^5$ targets using the SEQ ID NO:2/SEQ ID NO:4 primer pair was reduced 159-fold as compared to amplification using primer pairs which did not contain SEQ ID NO:2, and amplification of $10^3$ targets was reduced 31-fold. Amplification using SEQ ID NO:2/SEQ ID NO:5 was reduced 75-fold for $10^5$ targets and reduced about 14-fold for $10^3$ targets. This results was unexpected, as the sequence of SEQ ID NO:2 overlaps the other upstream amplification primers, all of which performed well in the amplification reaction. Based on these results, however, it was concluded that amplification using SEQ ID NO:2 was too insensitive to be useful for clinical diagnosis.

EXAMPLE 2

SEQ ID NO:1 and SEQ ID NO:4 were selected as the primer pair for further optimization in SDA reactions employing simultaneous amplification and detection, as described in EP 0 678 582. SDA was performed as in Example 1 except that 10 nM of $^{32}$P-labeled SEQ ID NO:8 was added prior to amplification as a signal primer. Secondary amplification products were detected on polyacrylamide gels as in Example 1. For comparison of amplification efficiency, SDA was also performed with post-amplification detection as in Example 1. Amplification levels were about equivalent for simultaneous amplification/detection and post-amplification detection, with an amplification factor of about $1 \times 10^{10}$.

SEQ ID NO:1 and SEQ ID NO:4 were then tested in simultaneous amplification/detection SDA reactions for specificity and cross reactivity: Target DNA from the following species was tested: *C. trachomatis* serovars A, B, Ba, C, D, E, F, G, I, J, K and L3; *C. psittaci, N. gonorrhea, N. meningititis, C. albicans* and *E. coli*. All *C. trachomatis* serovars tested ($10^4$ EBs/reaction) produced detectable amplification products. No signal above background was detected in any of the reactions containing DNA from non-*C. trachomatis* bacteria ($10^6$ EBs/reaction).

EXAMPLE 3

The sensitivity of detection of the *C. trachomatis* target sequence was tested using SEQ ID NO:1 and SEQ ID NO:4 in an assay employing a signal primer with post-amplification detection by fluorescence polarization as described by Walker, et al. (1996. *Clin. Chem.* 42, 9–13). SEQ ID NO:8 was labeled with 5-(4,6-dichlorotriazin-2-yl) amino fluorescein (5-DTAF) for use as a signal primer and added to the SDA reaction prior to amplification. The 50 µl amplification reactions contained 5 mM $MgCl_2$, 0.2 mM each dGTP, dATP and TTP, 1.4 mM α-thio-dCTP, 20 µg/ml non-acetylated bovine serum albumin, 1 ng/µl human placental DNA, 40 mM $K_iPO_4$ pH 7.6, 5% (v/v) glycerol, 3% (v/v) DMSO, 0.75 µM SEQ ID NO:1, 0.1875 µM SEQ ID NO:4, 10 nM 5-DTAF labeled SEQ ID NO:8, 0.075 µM SEQ ID NO:6 and SEQ ID NO:7, 3.2 units/µl BsoBI, 0.25 units/µl exonuclease deficient Bst DNA polymerase and varying amounts of Chlamydia EBs (0, 5, 10, 50, 500). An amplification reaction containing EDTA was used to inhibit amplification, representing a sample with no amplicon contamination and no target DNA Prior to addition of BsoBI, Bst polymerase, BSA and $MgCl_2$, the reactions (40 µl) were heated at 95° C. for 5 min. to denature the target DNA. After denaturing the target, the samples were allowed to equilibrate at 53.5° C. for 5 min. Amplification was initiated by addition of 10 µl of enzyme mix (5 µl 50 mM $MgCl_2$, 1 µl 1 mg/ml BSA, 1 µl of 25 units/µl Bst polymerase, 1 µl of 160 units/µl BsoBI and 2 µl 1X NEB2). After 30 min. of amplification, 45 µl of the reaction was diluted into 1 ml of fluorescence polarization buffer in a 12×75 borosilicate glass tube (Fisher) at 37° C. and fluorescence polarization (FP) was measured on an FPM-1 fluorometer (Jolley Research and Consultants) blanked against FP buffer. On the FPM-1, FP is measured by exciting the label in the vertical plane at 488 nm and measuring emission intensity in the vertical and horizontal planes at 520 nm. FP is expressed as millipolarization units (mP).

FP increased as the number of targets (EBs) in the amplification reaction increased (FIG. 1). Comparison of the 0 target sample with the EDTA sample shows slight contamination with about 10–20 amplicons. As few as five initial EBs could be detected over background.

EXAMPLE 4

The SEQ ID NO:1/SEQ ID NO:4 amplification primer pair was tested in a real-time SDA/fluorescence polarization detection system as described by Walker, et al. (1996) using an SLM 8100 fluorometer. This instrument has four cuvette chambers which can be read sequentially. Four 1 ml SDA reactions were performed with varying numbers of Chlamydia EBs ($10^6$, $10^4$, $10^2$ or 0) essentially as in Example 3. The 0 EB reaction also contained 10 µl of 0.5M EDTA to inhibit amplification, representing a sample lacking Chlamydia EBs and free of amplicon contamination. Amplification was detected in real-time at 53.5° C. The results are shown in FIG. 2. The reactions containing $10^6$ and $10^4$ EBs plateaued by 18 min. at an asymptotic FP value of approximately 215 mP. However, a quantitative difference between the samples could be seen, as the reactions containing higher initial target levels showed an increase in FP more quickly than reactions containing lower initial target levels. That is, the sample containing $10^6$ EBs began to show an increase in FP at 8 min., while the samples containing $10^4$ and $10^2$ EBs did not begin to show an increase in FP until 10 and 16 min., respectively.

---

What is claimed is:

1. pair of amplification primers comprising
   a) a first primer consisting of a target binding sequence selected from the group consisting of the target binding sequences of SEQ ID NO:1 and SEQ ID NO:3, and, optionally, a sequence required for an amplification reaction, and;
   b) a second primer consisting of a target binding sequence selected from the group consisting of the target binding sequences of SEQ ID NO:4 and SEQ ID NO:5, and, optionally, a sequence required for an amplification reaction.

2. The pair of amplification primers of claim 1 wherein the sequence required for the amplification reaction is a restriction endonuclease recognition site which is nicked by a restriction endonuclease during Strand Displacement Amplification.

3. The pair of amplification primers of claim 2 consisting of SEQ ID NO:1 and SEQ ID NO:3 or SEQ ID NO:4 and SEQ ID NO:5.

4. The pair of amplification primers of claim 1 further comprising an oligonucleotide selected from the group consisting of SEQ ID NO:6, SEQ ID NO:7 and SEQ ID NO:8.

5. A method for amplifying a target sequence of the *Chlamydia trachomatis* cryptic plasmid comprising:
   a) hybridizing to the target sequence
      i) a first amplification primer consisting of a target binding sequence selected from the group consisting of the target binding sequences of SEQ ID NO:1 and SEQ ID NO:3, and, optionally, a sequence required for an amplification reaction, and
      ii) a second amplification primer consisting of a target binding sequence selected from the group consisting of the target binding sequences of SEQ ID NO:4 and SEQ ID NO:5, and, optionally the sequence required for the amplification reaction, and;
   b) amplifying the target sequence by extending the hybridized first and second amplification primers on the target sequence.

6. The method of claim 5 further comprising detecting the amplified target sequence by hyridization to an assay probe.

7. The method of claim 6 wherein the assay probe consists of SEQ ID NO:8 tagged with a detectable label.

8. The method of claim 6 wherein the hybridized assay probe is extended by polymerase prior to detection of the label.

9. The method of claim 8 wherein the extended assay probe is detected by fluorescence polarization.

10. The method of claim 5 wherein the sequence required for the amplification reaction is a recognition site for a restriction endonuclease which is nicked by the restriction endonuclease during Strand Displacement Amplification.

11. The method of claim 10 wherein the first amplification primer consists of SEQ ID NO:1 or SEQ ID NO:3 and the second amplification primer consists of SEQ ID NO:4 or SEQ ID NO:5.

12. The method of claim 10 wherein the hybridized first and second amplification primers are displaced from the target sequence by extension of a first bumper primer consisting of SEQ ID NO:6 and a second bumper primer consisting of SEQ ID NO:7.

13. The method of claim 5 wherein the target sequence is amplified by the Polymerase Chain Reaction.

14. A method for amplifying a target sequence of the *Chlamydia trachomatis* cryptic plasmid comprising:
   a) hybridizing to the target sequence
      i) a first amplification primer consisting of SEQ ID NO:1 or SEQ ID NO:3, and
      ii) a second amplification primer consisting of SEQ ID NO:4 or SEQ ID NO:5, and;
   b) amplifying the target sequence in a Strand Displacement Amplification reaction.

15. The method of claim 14 further comprising detecting the amplified target sequence by hybridization to an assay probe.

16. The method of claim 15 wherein the assay probe consists of SEQ ID NO:8 tagged with a detectable label.

17. The method of claim 15 wherein the hybridized assay probe is extended by polymerase prior to detection.

18. The method of claim 17 wherein the extended assay probe is detected by fluorescence polarization.

19. The method of claim 14 wherein the first amplification primer consists of SEQ ID NO:1 and the second amplification primer consists of SEQ ID NO:4.

20. The method of claim 14 wherein the hybridized first and second amplification primers are displaced from the target nucleic acid by extension of a first bumper primer consisting of SEQ ID NO:6 and a second bumper primer consisting of SEQ ID NO:7.

21. A kit for species-specific detection of a *Chlamydia trachomatis* target sequence comprising:
   a) a first amplification primer comprising a target binding sequence selected from the group consisting of the target binding sequences of SEQ ID NO:1 and SEQ ID NO:3, and, optionally, a sequence required for an amplification reaction;
   b) a second amplification primer consisting of a target binding sequence selected from the group consisting of the target binding sequences of SEQ ID NO:4 and SEQ ID NO:5, and, optionally the sequence required for the amplification reaction, and;
   c) an assay probe for detecting the *Chlamydia trachomatis* target sequence.

22. The kit of claim 21 further comprising a reagent for amplification of the target sequence.

23. The kit of claim 22 further comprising a reagent for detection of the assay probe.

* * * * *

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

ACCGCATCGA ATCGATGTCT CGGGTAGAAA ATCGCATGCA AGATA          45

( 2 ) INFORMATION FOR SEQ ID NO:2:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

ACCGCATCGA ATCGATGTCT CGGGCGCATG CAAGATATCG AGTAT          45

( 2 ) INFORMATION FOR SEQ ID NO:3:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

ACGCCATCGA ATCGATGTCT CGGGATGCAA GATATCGAGT ATGCG          45

(2) INFORMATION FOR SEQ ID NO:4:

(i) SEQUENCE CHARACTERISTICS:
       (A) LENGTH: 46 base pairs
       (B) TYPE: nucleic acid
       (C) STRANDEDNESS: single
       (D) TOPOLOGY: linear (xi) SEQUENCE DESCRIPTION: SEQ ID NO:4:

CGATTCCGCT CCAGACTTCT CGGGAGCTGC CTCAGAATAT ACTCAG     46

(2) INFORMATION FOR SEQ ID NO:5:

(i) SEQUENCE CHARACTERISTICS:
       (A) LENGTH: 45 base pairs
       (B) TYPE: nucleic acid
       (C) STRANDEDNESS: single
       (D) TOPOLOGY: linear (xi) SEQUENCE DESCRIPTION: SEQ ID NO:5:

CGATTCCGCT CCAGACTTCT CGGGGCAAGC TGCCTCAGAA TATAC     45

(2) INFORMATION FOR SEQ ID NO:6:

(i) SEQUENCE CHARACTERISTICS:
       (A) LENGTH: 21 base pairs
       (B) TYPE: nucleic acid
       (C) STRANDEDNESS: single
       (D) TOPOLOGY: linear (xi) SEQUENCE DESCRIPTION: SEQ ID NO:6:

TAAACATGAA AACTCGTTCC G     21

(2) INFORMATION FOR SEQ ID NO:7:

(i) SEQUENCE CHARACTERISTICS:
       (A) LENGTH: 26 base pairs
       (B) TYPE: nucleic acid
       (C) STRANDEDNESS: single
       (D) TOPOLOGY: linear (xi) SEQUENCE DESCRIPTION: SEQ ID NO:7:

TTTTATGATG AGAACACTTA AACTCA     26

(2) INFORMATION FOR SEQ ID NO:8:

(i) SEQUENCE CHARACTERISTICS:
       (A) LENGTH: 34 base pairs
       (B) TYPE: nucleic acid
       (C) STRANDEDNESS: single
       (D) TOPOLOGY: linear (xi) SEQUENCE DESCRIPTION: SEQ ID NO:8:

TAGAGTCTTC AAATATCAGA GCTTTACCTA ACAA     34